United States Patent [19]

Barry et al.

[11] Patent Number: 5,142,085

[45] Date of Patent: Aug. 25, 1992

[54] PREPARATION OF (CYANOFLUOROMETHYL)-PHOSPHONATES

[75] Inventors: Jean-Marc Barry, Paris; Serge Droux, Dammartin en Coele; Giuseppe Gigliotti, Paris, all of France

[73] Assignee: Roussel Uclaf, Paris, France

[21] Appl. No.: 743,859

[22] Filed: Aug. 12, 1991

[30] Foreign Application Priority Data

Aug. 14, 1990 [FR] France ................ 90 10324

[51] Int. Cl.⁵ ............................ C07F 9/40
[52] U.S. Cl. ................... 558/167; 558/166; 558/311; 558/313
[58] Field of Search ............... 558/166, 167, 311, 313

[56] References Cited

U.S. PATENT DOCUMENTS

| | | | |
|---|---|---|---|
| 1,828,267 | 10/1931 | Wilcke | 558/313 |
| 1,876,652 | 9/1932 | Fischl et al. | 558/313 |
| 2,389,217 | 11/1945 | Surrey | 558/313 |
| 3,360,541 | 12/1967 | Korchinsky et al. | 558/313 |
| 4,757,127 | 7/1988 | Tessier et al. | 558/231 |

OTHER PUBLICATIONS

Weygand-Hilgetag, "Preparative Organic Chemistry" (1972), pp. 488-489; John Wiley & Sons.

Noller "Chemistry of Organic Compounds", 3rd Ed., (1965), pp. 196 and 268; W. B. Saunders & Co.
Chemistry of Organic Fluorine Compounds, 2nd ed. (1976), p. 231; John Wiley & Sons.

Primary Examiner—Joseph Paul Brust
Attorney, Agent, or Firm—Bierman and Muserlian

[57] ABSTRACT

A process for the preparation of a compound of the formula

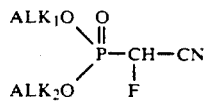

wherein $alk_1$ and $alk_2$ are individually alkyl of 1 to 8 carbon atoms comprising reacting a compound of the formula

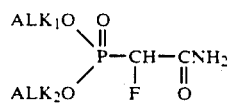

with a dehydrating agent to obtain the corresponding compound of formula I.

2 Claims, No Drawings

PREPARATION OF (CYANOFLUOROMETHYL)-PHOSPHONATES

THE INVENTION

The process of the invention for the preparation of a compound of the formula $$\begin{array}{c} ALK_1O \\ \diagdown \\ ALK_2O \end{array} P \begin{array}{c} O \\ \parallel \\ -CH-CN \\ | \\ F \end{array} \qquad I$$

wherein $alk_1$ and $alk_2$ are individually alkyl of 1 to 8 carbon atoms comprises reacting a compound of the formula $$\begin{array}{c} ALK_1O \\ \diagdown \\ ALK_2O \end{array} P \begin{array}{c} O \\ \parallel \\ -CH-CNH_2 \\ | \quad \parallel \\ F \quad O \end{array} \qquad II$$

with a dehydrating agent to obtain the corresponding compound of formula I.

The dehydration agent is preferably phosphorus oxychloride, thionyl chloride or methane sulfonyl chloride and the reaction is preferably effected in the presence of an organic base. The preferred dehydration agent is phosphorus oxychloride.

Since the preferred dehydration agent contains a halogen, especially chlorine, a transhalogenation reaction with fluorine could be expected. Surprisingly, this does not occur.

Examples of $alk_1$ and $alk_2$ are methyl, ethyl, n-propyl, isopropyl and n-butyl, but ethyl is preferred. The compounds of formula I are known in European Patent No. 0.224,417 as being useful in the synthesis of fluorocyano vinyl pyrethrinoid derivatives of European Patent No. 0.133,406. They are also useful in the synthesis of fluorinated products which are inhibitors of HMG-CoA reductase which is 3-hydroxy-3-methyl-glutaryl coenzyme A which has pharmaceutical properties.

The compounds of formula II may be prepared by reacting a compound of the formula $$\begin{array}{c} ALK_1O \\ \diagdown \\ ALK_2O \end{array} P \begin{array}{c} O \quad\quad O \\ \parallel \quad\quad \parallel \\ -CH-C-OALK_3 \\ | \\ F \end{array} \qquad III$$

wherein $alk_1$, $alk_2$ and $alk_3$ are individually alkyl of 1 to 8 carbon atoms with an amidification agent. Preferably $alk_3$ is methyl, ethyl, n-propyl, isopropyl, n-butyl or isobutyl and the amidification agent is ammonium hydroxide. This reaction is preferably effected at $-20°$ to $30°$ C.

The process for the preparation of the compounds of formula II surprisingly gives excellent yields as a reaction between the fluorine and the amidification agent could be expected to form, for example, ammonium fluoride when using ammonium hydroxide. The product of formula II is obtained in excellent yield and purity.

European Patent No. 0.224,417 describes a fluorination process to prepare the compounds of formula III as follows:

$$\begin{array}{c} N\equiv C \\ \diagdown \\ C-P \\ \parallel \\ Na^-O^- \end{array} \begin{array}{c} O \quad OEt \\ \parallel / \\ \diagdown \\ OEt \\ H \end{array} \xrightarrow{F_2} \begin{array}{c} F \\ \diagdown \\ C-P \\ / \\ N\equiv C \end{array} \begin{array}{c} O \quad OEt \\ \parallel / \\ \diagdown \\ OEt \end{array}$$

Various preparation processes for fluorinated derivatives of phosphoric acid are also known such as the processes described in J. Med. Chem. 1980, Vol. 23, 1077–1083, CA 741971, 124736, in J. Chem. Research (5) 1985 p. 92–93 and European Patent No. 50,534. These processes require the use of perchloryl fluoride which particularly on the industrial level, is not conceivable due to the risks of violent explosions that it entails. As for the use of fluorine gas, even diluted with nitrogen, it involves specific installations and by the same token, significant production costs. The process of the invention has the advantage of avoiding the handling of fluorine and perchloryl fluoride, since the fluorine is already in place in the products of formula III.

Moreover, the process of the invention has the advantage of using reagents and solvents which are commonly available and inexpensive. Its use therefore allows the industrial preparation of the compounds of formula I.

The products of formula III may be prepared very simply, starting from the products of the formula $$\begin{array}{c} Br \\ \diagdown \\ CH-C-alk_3 \\ / \\ F \end{array} \qquad IV$$

which are commercial products and an appropriate phosphite. For example, methyl bromo-fluoro-acetate can be reacted by the following process:

$$\begin{array}{c} Br \\ \diagdown \\ F \end{array} CO_2Me \xrightarrow{P(Oalk)_3} \begin{array}{c} alk-O \\ \diagdown \\ / \\ alk-O \quad O \end{array} P \begin{array}{c} CO_2Me \\ \diagdown \\ F \end{array}$$

alk is alkyl (Guita Etemad - Moghadam et al. Bull Soc. Chim. Fr, 1985, p. 448–54).

In the following example, there is described a preferred embodiment to illustrate the invention. However, it is to be understood that the invention is not intended to be limited to this specific embodiment.

EXAMPLE

Diethyl ester of (cyanofluoromethyl) phosphonic acid

Stage A: Diethyl ester of [(aminocarbonyl)-fluoromethyl]phosphonic acid 700 ml of 22°Be ammonium hydroxide were introduced at 5 to 10° C. into 664 g of methyl (diethoxyphosphinyl) fluoro acetate under nitrogen and with stirring and the reaction mixture was stirred for 3 hours. The excess ammonium hydroxide was distilled off under reduced pressure and the reaction medium was saturated with sodium chloride Extraction took place with methylene chloride and the extracts were washed with a saturated solution of sodium chloride The organic phase was dried, filtered and evaporated to dryness under reduced pressure The 646 g of residue were dissolved in 1 liter of methylene chloride and distillation took place under reduced pressure at a constant volume by replacing the methylene chloride with isopropyl ether. After separating, washing and drying, 551.4 g of the desired product were obtained.

| Microanalysis: $C_6H_{13}O_4FNP$ | | | | |
|---|---|---|---|---|
| | % C | % H | % N | % P |
| calculated | 33.8 | 6.15 | 6.57 | 14.53 |
| found | 33.8 | 6.2 | 6.5 | 14.3 |
| IR Spectrum: ($CHCl_3$) | | | | |
| =C—NH2 | | | 3530 cm$^{-1}$ | |
| | | | 3496 cm$^{-1}$ | |
| | | | 3416 cm$^{-1}$ | |
| $\diagdown$C=O | | | 1710 cm$^{-1}$ | |
| NH2 | | | 1580 cm$^{-1}$ | |
| NMR spectrum CDCl$_3$ | | | | |
| H of the ethyls | | | 1.36 ppm and 4.25 ppm | |
| H of —CH—F | | | 5.19 ppm | |

Stage B: Diethyl ester of [cyanofluoromethyl]phosphonic acid 480 ml of phosphorus oxychloride were added at 60° to 70° C. to a solution of 359 g of the product of step A and 1900 ml of 1,2-dichloroethane and the reaction mixture was stirred for 3 hours at 67° to 70° C. The temperature was returned to 20° C. and the mixture was poured into 10 liters of a saturated aqueous solution of NaHCO$_3$ followed by decanting and evaporating to dryness under reduced pressure. The residue was chromatographed on silica eluting with a hexane-ethyl acetate (1-1) mixture to obtain 168 g of the desired product.

| IR Spectrum: CHCl$_3$ | |
|---|---|
| 1278 cm$^{-1}$ | 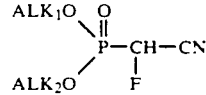 |
| 2250 cm$^{-1}$ | —C≡N |
| NMR Spectrum: Proton CDCl$_3$ 300 MHz | |
| H of the ethyls | 1.43 and 4.35 ppm |
| H of P<u>C</u>H—F | 5.40 ppm |

NMR $^{31}$P CDCl$_3$ 300 MHz
6.56 ($J_{PF}$=69.5 Hz).
NMR $^{19}$F CDCl$_3$ 300 MHz
215.5 ($J_{HF}$=46 Hz;
$J_{PF}$=69.5 Hz).

Various modifications of the process of the invention may be made without departing from the spirit or scope thereof and it is to be understood that the invention is intended to be limited only as defined in the appended claims.

What is claimed is:

1. A process for the preparation of a compound of the formula

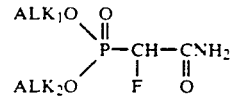

wherein alk$_1$ and alk$_2$ are individually alkyl of 1 to 8 carbon atoms comprising reacting a compound of the formula $$\begin{array}{c} ALK_1O \\ \diagdown \\ ALK_2O \end{array} \!\!\! \begin{array}{c} O \\ \| \\ P-CH-CNH_2 \\ | \quad \| \\ F \quad O \end{array} \qquad II$$

with a phosphorus oxychloride to obtain the corresponding compound of formula I.

2. The process of claim 1 wherein alk$_1$ and alk$_2$ are ethyl.

* * * * *